(12) United States Patent
Mosser et al.

(10) Patent No.: US 6,660,266 B1
(45) Date of Patent: Dec. 9, 2003

(54) REVERSAL OF PROINFLAMMATORY RESPONSE BY LIGATING THE MACROPHAGE FCγRI RECEPTOR

(75) Inventors: David M. Mosser, Hyattsville, MD (US); Fayyaz Sutterwala, Northford, CT (US)

(73) Assignee: Temple University - of The Commonwealth System of Higher Education, Philadelphia, PA (US)

( * ) Notice: Subject to any disclaimer, the term of this patent is extended or adjusted under 35 U.S.C. 154(b) by 10 days.

(21) Appl. No.: 09/692,586

(22) Filed: Oct. 19, 2000

Related U.S. Application Data

(63) Continuation of application No. PCT/US99/09269, filed on Apr. 29, 1999.
(60) Provisional application No. 60/084,385, filed on May 6, 1998.

(51) Int. Cl.[7] ...................... A61K 39/395; A61K 39/42; C07K 16/00
(52) U.S. Cl. ................ 424/130.1; 424/143.1; 424/144.1; 424/184.1; 530/387.1
(58) Field of Search ............. 424/130.1, 143.1, 424/144.1, 184.1; 530/387.1

(56) References Cited

U.S. PATENT DOCUMENTS 5,877,396 A * 3/1999 Ravetch et al.

OTHER PUBLICATIONS

Ngo et al, in The Protein Folding Problem and Tertiary Structure Prediction, 1994. (ed.), Birkhauser, Boston, MA, pp. 433 and 492–495.*
Coleman et al. (Research in Immunology, 1994; 145(1): 33–36).*
Abaza et al. (Journal of Protein Chemistry, vol. 11, No. 5, 1992, pp. 433–444).*
Sundaram et al. (J. Leukocyte Biology 1993; 54:81–88).*
Cruse et al. (Illustrated Dictionary of Immunology, New York, CRC Press, 1995, pp. 166 and 169).*
Chougnet et al. (J. Infectious Diseases 1996; 174: 46–53).*
Liew (Nature Reviews, Immunology 2002; 2: 55–60).*
Campbell (Laboratory Techniques in Biochemistry and Molecular Biology, Elsevier Science Publishers, 1984, pp. 1–32).*
Ratcliffe et al. (Immunol. Letters 1983; 7(2): 73–76).*
Philip Cohen (Fundamental Immunology, Lippencott–Raven Publishers, Philadelphia, 1999, pp. 1067–1088).*
Fayyaz Sutterwala, et al., *Selective Suppression of Interleukin–12 Induction After Macrophage Receptor Ligation*, J. Exp. Med., vol. 185, Jun. 2, 1997, pp 1977–1985.
Donald L. Tankersley, *Dimer Formation In immunoglobulin Preparations and Speculations On The Mechanism Of Action of Intravenous Immune Globulin in Autoimmune Diseases*, Immunological Reviews, 1994, No. 139, pp 159–172.
Paul Vialtel, et al., *Nucleation–controlled Polymerization of human Monoclonal Immunoglobulin G Cryoglobulins*, The Journal of Biological Chemistry, vol. 257 No. 7,1982, pp 3811–3818.
John K. Lee, et al., *Determination Of the Molecular Size Distribution of Immunoglobulin G (IgG) In Intravenous IgG–Albumin Formulations By High–Performance Liquid Chromatography*, Journal of Chromatography, 444, 1988, pp 141–152.
J. Keith Wright, et al., *Dimeric, Trimeric and Tetrameric Complex of Immunoglobulin G Fix Complement*, Biochem. J., 187, 1980, pp 775–780.
Amanda 1. Gavin, et al.,*Cutting Edge: identification Of The Mouse IgG3 Receptor: Implications For Antibody Effector Function At the Interface Between Innate and Adaptive Immunity*, J. Immunol., Jan. 1, 1998; 160 (1), pp 20–23.
Deo, et al., *Clinical Significance Of IgG Fc Receptors and FcγR–Directed Immunotherapies*, Immunology today, Mar. 1997, vol. 18, pp 127–135.
Fayyaz Sutterwala, et al., *Reversal of Proinflammatory Responses By Ligating the macrophage Fcγ Receptor Type I*, Journal of Experimental Medicine, Jul. 6, 1998, vol. 188, No. 1, pp 217–222.

* cited by examiner

Primary Examiner—Christina Chan
Assistant Examiner—Michail A. Belyavski
(74) Attorney, Agent, or Firm—Drinker Biddle & Reath LLP

(57) ABSTRACT

Ligation of the Fcγ receptor type I (FcγRI) on IL-10-producing cells leads to a selective upregulation of IL-10 production, which in turn induces a marked suppression of IL-12 biosynthesis by IL-12-producing cells, particularly macrophages. The ligation of the FcγRI receptor thus downmodulates IL-12 production via a mechanism that is dependent on macrophage-derived IL-10. Agents for ligating FcγRI comprise, for example, multivalent antibodies which bind the FcγRI receptor, immune complexes comprising antibodies which contain the Fc region of IgG, and IgG multimers, preferably IgG dimers and trimers. The ligating agent may be administered to therapeutically inhibit proinflammatory immune responses. In particular, the ligating agent may be administered to treat or prevent endotoxic shock associated with bacterial endotoxemia, and to treating autoimmune disorders.

10 Claims, 10 Drawing Sheets

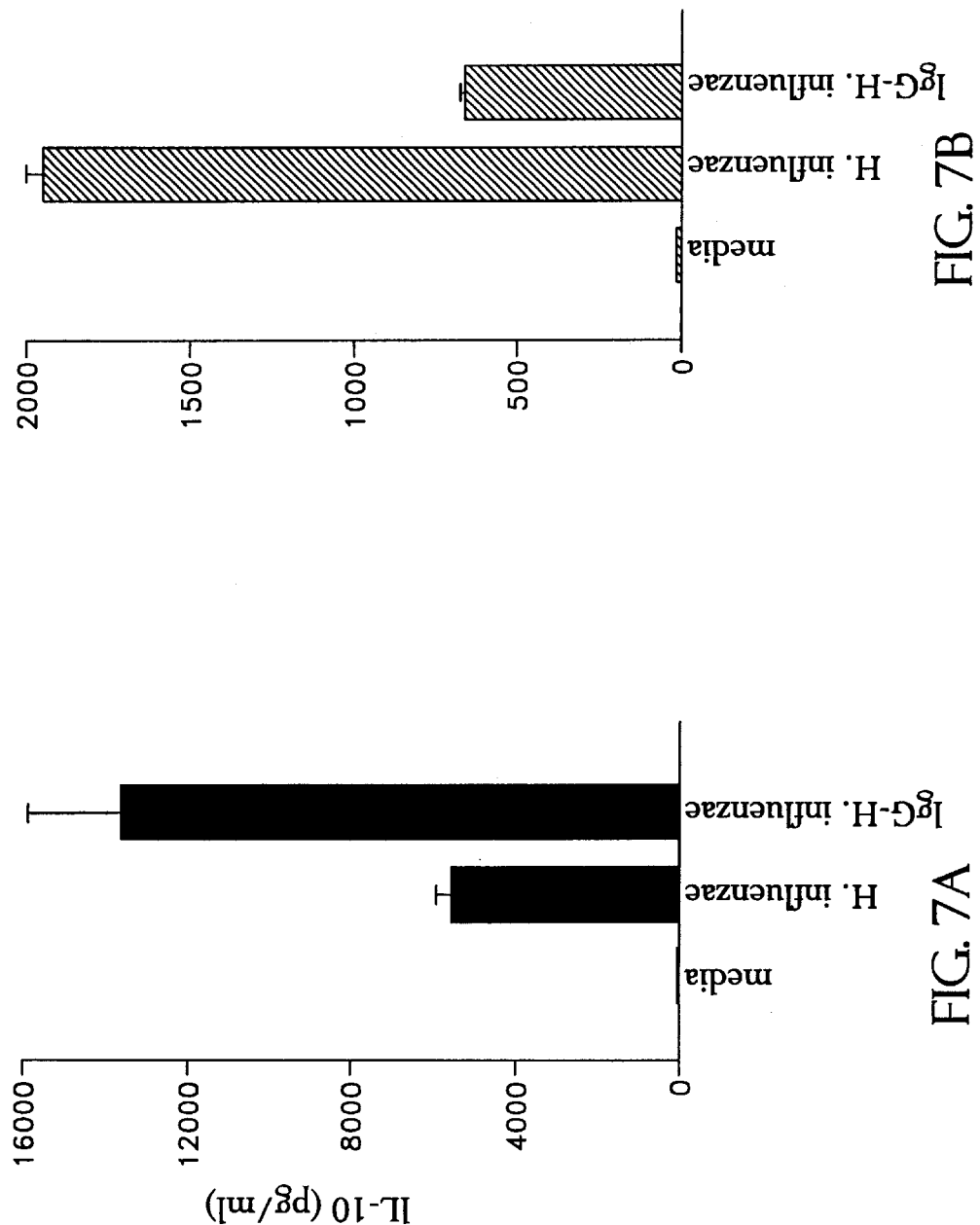

US 6,660,266 B1

REVERSAL OF PROINFLAMMATORY RESPONSE BY LIGATING THE MACROPHAGE FCγRI RECEPTOR

CROSS REFERENCE TO RELATED APPLICATIONS

This application is a continuation of international application number PCT/US99/09269, filed Apr. 29, 1999, which claims the benefit under 35 U.S.C. 119(e) of provisional application Serial No. 60/084,385, filed May 6, 1998, now abandoned.

REFERENCE TO GOVERNMENT GRANT

The invention described herein was supported in part by National Institutes of Health grant AI24313. The Federal government has certain rights in the invention.

FIELD OF THE INVENTION

The invention relates to the therapeutic modulation of inflammatory response modulation, and in particular to the suppression of macrophage proinflammatory responses to infectious and/or inflammatory stimuli.

BACKGROUND OF THE INVENTION

Macrophages are prodigious secretory cells which can produce a number of molecules which can either potentiate or dampen immune responses (Nathan, *J. Clin. Invest.* 79:319–322, 1987). In response to infectious or inflammatory stimuli, macrophages can produce several proinflammatory molecules, including TNFα, IL-1, IL-6 and IL-12 (Nathan, *J. Clin. Invest.* 79:319–322, 1987; Trinchieri et al., *J. Leukocyte Biol.* 59:505–511, 1996). These proinflammatory molecules are important for host defense, because experimentally infected animals deficient in these cytokines are invariably more susceptible to acute bacterial infections than are normal animals (Dalrymple et al., *Infect. Immun.* 63:2262–2268, 1995; Kincy-Cain et al., *Infect. Immun.* 64:1437–1440, 1996).

IL-12 is a 70 kDa heterodimer consisting of two covalently linked polypeptide chains, one of 35 kDa (p35) and the other of 40 kDa (p40). IL-12 plays an important role in the development of $T_H1$-type immune responses (Trinchieri et al., *J. Leukocyte Biol.* 59:505–511, 1996). This cytokine is a potent inducer of IFNγ from T and NK cells, and it has been shown to play a crucial role in the development of immunity to intracellular pathogens (Heinzel et al., *J. Exp. Med.* 177:1505–1512, 1993; Tripp et al., *Proc. Nat. Acad. Sci. USA* 90:3725–3729, 1993).

IL-12 is a potent inducer of cell-mediated immune responses, and animals lacking IL-12 are invariably more susceptible to infections with intracellular pathogens (Mattner et al., *Eur. J. Immunol.* 26:1553–1559, 1996). It has been recently demonstrated that some microbes can influence IL-12 production by macrophages. Leishmania major, measles virus, and HIV have all been shown to downregulate the production of IL-12 by macrophages or monocytes infected with them (Carrera et al., *J. Exp. Med.* 183:515–526, 1996; Karp et al., *Science* 273:228–231, 1996; Chehimi et al., *J. Exp. Med.* 179:1361–1366, 1994). This downmodulation of IL-12 has the potential of providing these pathogens with a means of suppressing the development of cell-mediated immunity.

The production of proinflammatory cytokines such as IL-12, however, must be tightly regulated, since their production is also correlated with many of the pathologies associated with acute sepsis or with autoimmune diseases. The overproduction of IL-12 during an immune response, however, has the potential to be detrimental to the host. IL-12 produced during endotoxemia (Wysocka et al., *Eur. J. Immunol.* 25:672–676, 1995), and during a number of autoimmune disorders, including insulin-dependent diabetes mellitus (Trembleau et al., *J. Exp. Med.* 181:817–821, 1995), experimental allergic encephalomyelitis (Leonard et al., *J. Exp. Med.* 181:381–386, 1995), or collagen-induced arthritis (Germann et al., *Proc. Natl. Acad. Sci. USA* 92:4823–4827, 1995), can lead to exacerbated disease.

In many instances, macrophages can participate in the regulation of proinflammatory cytokines by the production of anti-inflammatory molecules. The secretion of prostaglandins, TGFβ, and IL-10 by macrophages has been associated with anti-inflammatory responses (Tsunawaki et al., *Nature* 334:260–262, 1988; Bogdan et al., *J. Exp. Med.* 174:1549–1555, 1991; Kunkel et al., *J. Biol. Chem.* 263:5380–5384, 1988). These anti-inflammatory molecules have the potential to ameliorate the potentially deleterious effects of an overly aggressive immune response. Thus, the balance between the secretion of pro- and anti-inflammatory molecules by macrophages is a critical component of the acute phase response and has the potential to affect the adaptive immune response that subsequently develops.

Interleukin-10 (IL-10) is an 18 kDa cytokine produced by the $T_H2$ subset of CD4+ helper cells. It is also produced by some activated B cells, by some $T_H1$ cells (in humans), by activated macrophages, and by some non-lymphocytic cell types (e.g., keratinocytes). In contrast to IL-12, IL-10 has been associated with an inhibition of $T_H1$-type immune responses. IL-10 has been shown to inhibit the production of $T_H1$ cytokines and the proliferation of $T_H1$ cells to antigen (Malefyt et al., *J. Exp. Med.* 174:915–924, 1991; Fiorentino et al., *J. Immunol.* 146:3444–3451, 1991). IL-10 inhibits IL-12 production by macrophages (D'Andrea et al., *J. Exp. Med.* 178:1041–1048, 1993), and the administration of exogenous IL-10 can diminish the toxicity of LPS (Howard et al., *J. Exp. Med.* 177:1205–1208, 1993; Berg et al., *J. Clin. Invest.* 96:2339–2347, 1995). IL-10 has been considered for the treatment of autoimmune diseases such as arthritis (Hart et al., *Immunology* 84:536–542, 1995) and colitis (Davidson et al., *J. Exp. Med.* 184:241–251, 1996).

The Fcγ receptor (FcγR) is a receptor for the Fc region of IgG. B and T lymphocytes, natural killer cells, polymorphonuclear leukocytes, mononuclear phagocytes, and platelets contain Fcγ receptor. The three types of Fcγ receptors include FcγRI (CD64), FcγRII (CD32) and FcγRIII (CD16). CD16, the FcγRIII, is the prototypical proinflammatory Fc receptor. Ligating FcγRIII has been associated with the production of proinflammatory cytokines (Cassatella et al., *J. Exp. Med.* 169:549–567, 1989), and mice lacking FcγRIII undergo diminished Arthus reactions (Hazenbos et al., *Immunity* 5:181–188, 1996). CD32, the FcγRII, is a negative regulator of immune complex-triggered immune responses, and mice lacking FcγRII have augmented anaphylactic responses to IgG (Takai et al., *Nature* 379:346–349, 1996). FcγRI represents a high-affinity receptor found on mononuclear phagocytes. In humans, its binds IgG1 and IgG3. FcγRII and FcγRIII are low-affinity IgG receptors.

A mechanism whereby receptor ligation can downmodulate IL-12 production by macrophages has been described (Sutterwala et al., *J. Exp. Med.* 185:1977–1985 (1997). However, this previously described mechanism of IL-12 downregulation did not exhibit specificity with regard to the macrophage phagocytic receptors that could induce this downmodulation.

Lipopolysaccharide endotoxin (LPS) is a complex macromolecule from the cell walls of certain bacteria, some of which cause diseases like typhoid fever, dysentery, and urinary tract infections and from other bacteria which are common inhabitants of animal and human intestinal tracts but ordinarily do not cause disease. All of these bacteria have in common the same type of cell wall and are classified as Gram-negative. LPS induces the production and release of immunologically active cytokines and other mediators of the proinflammatory response.

There are many pathophysiological effects of LPS, one of which is endotoxemia or septic shock which results from large amounts of endotoxin in the blood. The majority of the cases of septic shock are a consequence of Gram-negative bacteremia (bacteria in the blood). However, the septic shock syndrome can be induced by other organisms including Gram-positive bacteria and fungi. A key factor in the development of toxic shock is the release of LPS from Gram-negative bacteria and the subsequent effects of the endotoxin on various cells in the body which become highly activated. As a result, the host is overwhelmed with many cell substances that lead to circulatory failure, shock and death.

There is a need for a therapeutic modality which is capable of reversing the proinflammatory responses of macrophages to stimuli such as bacteria and bacterial products, and stimuli associated with autoimmune disease. There is needed a therapeutic modality which is capable of inhibiting host proinflammatory immune responses while at the same time inducing host anti-inflammatory responses. In particular what is needed is a modality for dampening the acute response to inflammatory stimuli, such as LPS or Gram-negative bacteria. Such therapeutic modalities would be useful in treating various proinflammatory diseases such as autoimmune disorders and bacteremia caused by gram-negative bacilli.

SUMMARY OF THE INVENTION

A method for enhancing IL-10 production by FcγRI receptor-expressing cells of a mammal is provided. An agent is administered to the mammal, which agent either alone or in combination with one or more substances in the body of the mammal, causes ligation of the FcγRI receptors on those FcγRI receptor-expressing cells. The mammal may be a human being. The cells most particularly comprise macrophages.

According to one embodiment, the administered agent is a ligating agent comprising a multivalent antibody which binds to the FcγRI receptor.

According to another embodiment, the ligating agent comprises an immune complex containing at least two antibody molecules or fragments thereof which contain the Fc region of IgG.

According to yet another embodiment of the invention, the ligating agent comprises an antibody multimer containing at least two antibody molecules or fragments thereof which contain the Fc region of IgG. Preferably, the ligating agent comprises a preparation of IgG comprising IgG dimers, trimers or a mixture thereof. The IgG content of the preparation preferably comprises, on a weight percent basis, at least about 50% IgG dimers, trimers, or a mixture thereof.

A method of inhibiting a proinflammatory immune response in a mammal is provided comprising administering an effective amount of the ligating agent to the mammal to cause ligation of FcγRI receptors on cells of the mammal.

According to another embodiment of the invention, a method of inhibiting a proinflammatory immune response in a mammal is provided. An IgG antibody is administered, which binds to antigen in the mammal to form an immune complex capable of ligating FcγRI receptors present on host cells.

According to another embodiment of the invention, a method for treating or preventing shock associated with bacterial endotoxemia, or for treating an autoimmune disorder, is provided. An effective amount of a ligating agent is administered to a mammal in need of such treatment. The ligating agent causes ligation of FcγRI receptors on cells of the mammal.

According to another embodiment of the invention, a method is provided for treating or preventing shock associated with bacterial endotoxemia in a mammalian host. An IgG antibody is administered, which binds to antigen in the host to form an immune complex capable of ligating FcγRI receptors present on host cells.

According to another embodiment of the invention, a method for treating an autoimmune disorder in a mammalian host is provided, comprising administering an IgG antibody which binds to antigen in the host to form an immune complex capable of ligating FcγRI receptors present on host cells.

Figure 6A:
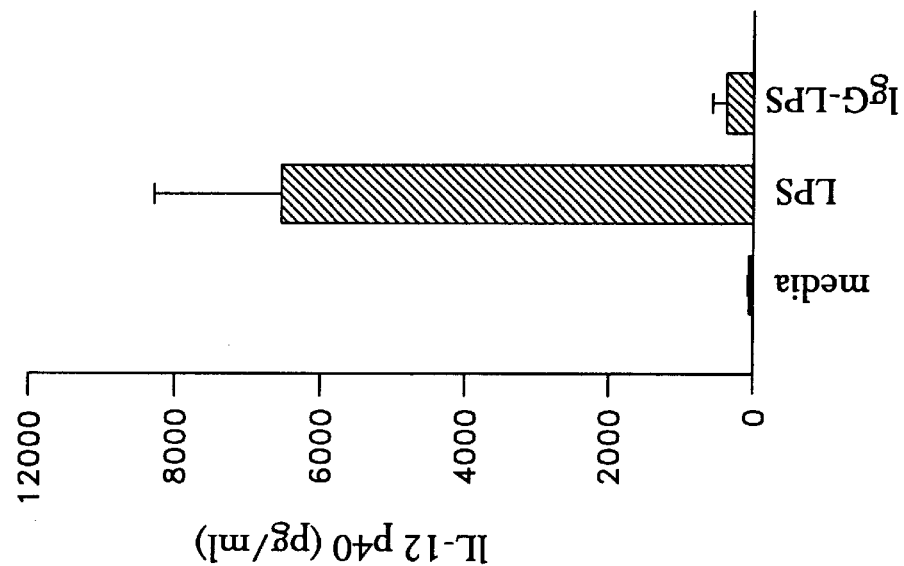

FIG. 6A is a graph of the ELISA determination of IL-10 in the supernatant of BMMΦ exposed to either media, LPS, or IgG-LPS.

Figure 6B:
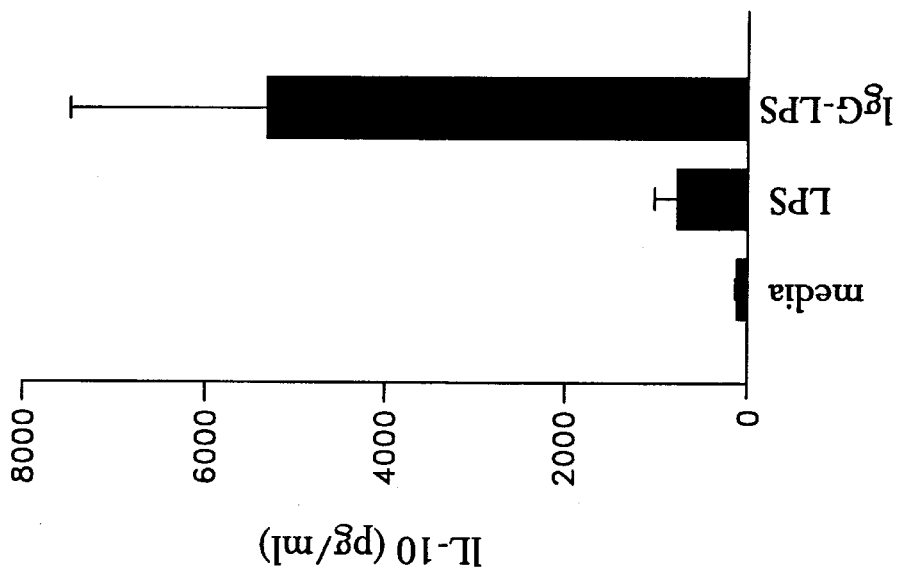

FIG. 6B is a graph of the ELISA determination of IL-12(p40) in the supernatant of BMMΦ exposed to either media, LPS, or IgG-LPS.

FIG. 7A is a graph of the ELISA determination of IL-10 in the supernatant of BMMΦ incubated with media alone or with unopsonized or IgG-opsonized *H. Influenzae*.

FIG. 7B is a graph of the ELISA determination of IL-12(p40) in the supernatant of BMMΦ incubated with media alone or with unopsonized or IgG-opsonized *H. Influenzae*.

Figure 8A:
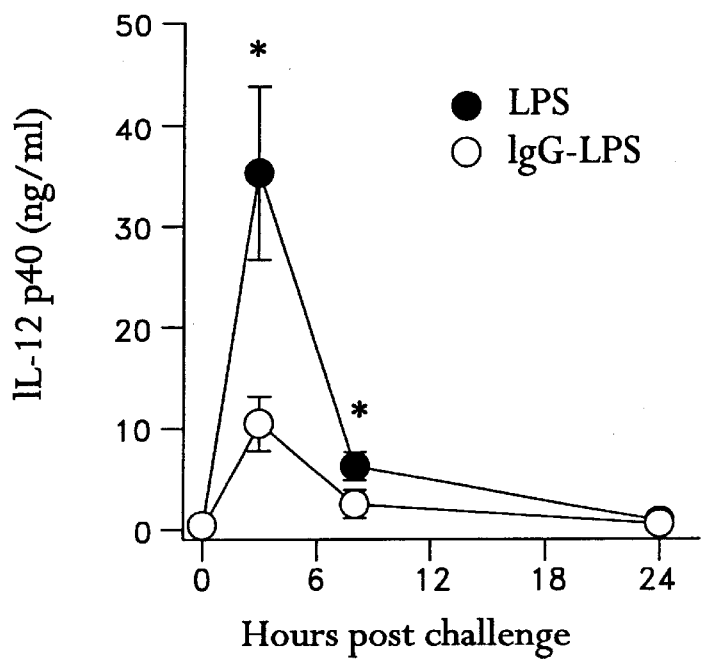

FIG. 8A is a plot of IL-12(p40) serum levels in RAG-1$^{-/-}$ mice which received either LPS or IgG-LPS intravenously at a final LPS dose of 4 μg. Serum levels were measured at the indicated times post-challenge.

Figure 8B:
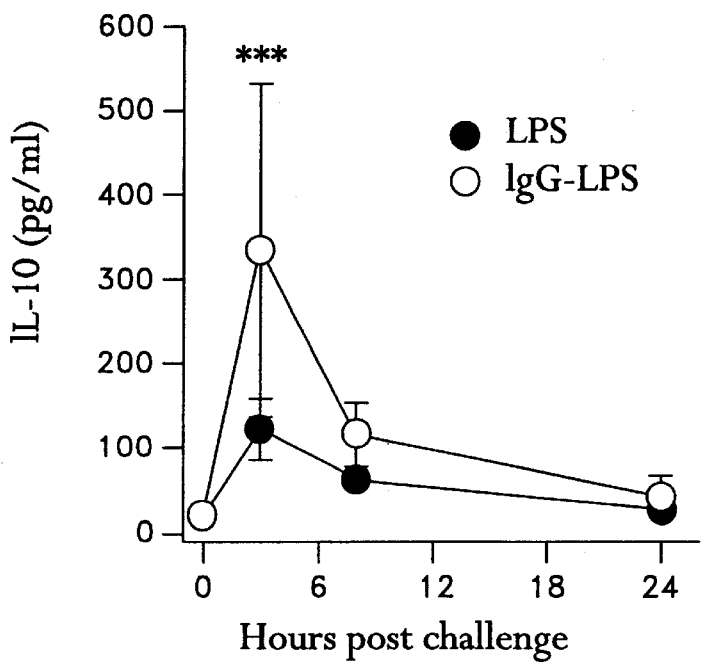

FIG. 8B is a plot of IL-10 serum levels in RAG-1$^{-/-}$ mice which received either LPS or IgG-LPS intravenously at a final LPS dose of 4 μg. Serum levels were measured at the indicated times post-challenge.

Figure 9A:
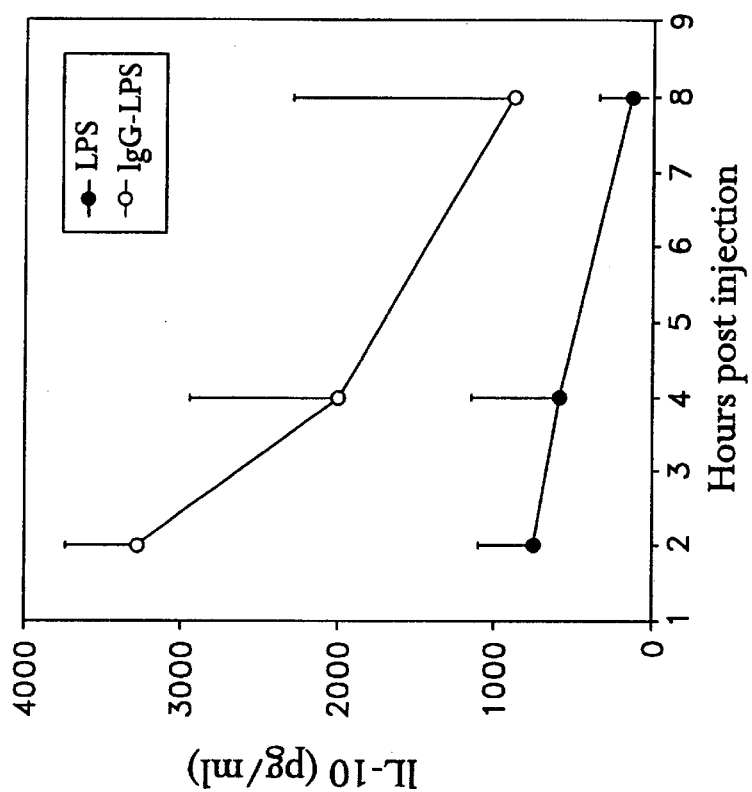

FIG. 9A is similar to FIG. 8A, with IL-12(p40) serum levels sampled at 2, 4 and 8 hours.

Figure 9B:
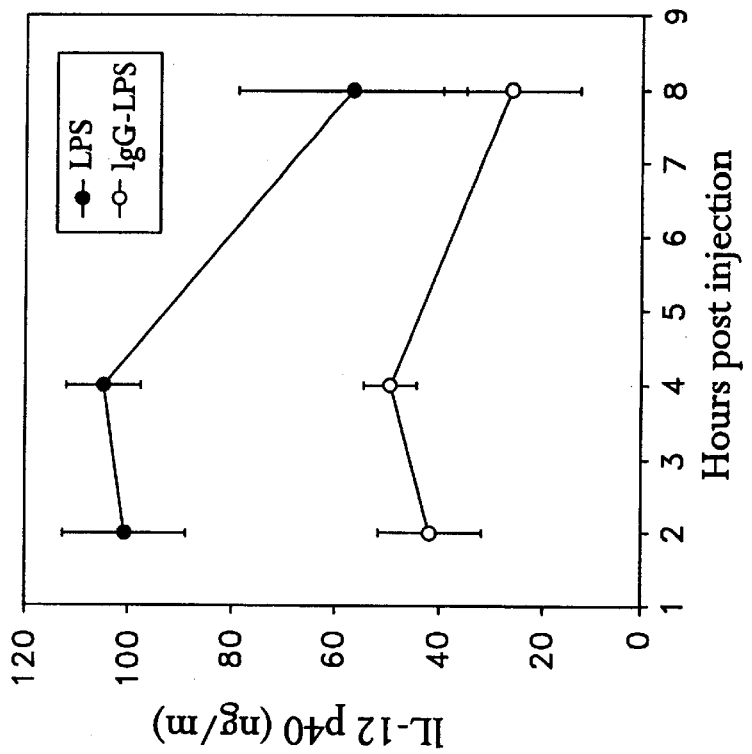

FIG. 9B is similar to FIG. 8B, with IL-10 serum levels sampled at 2, 4 and 8 hours.

Figure 10B:
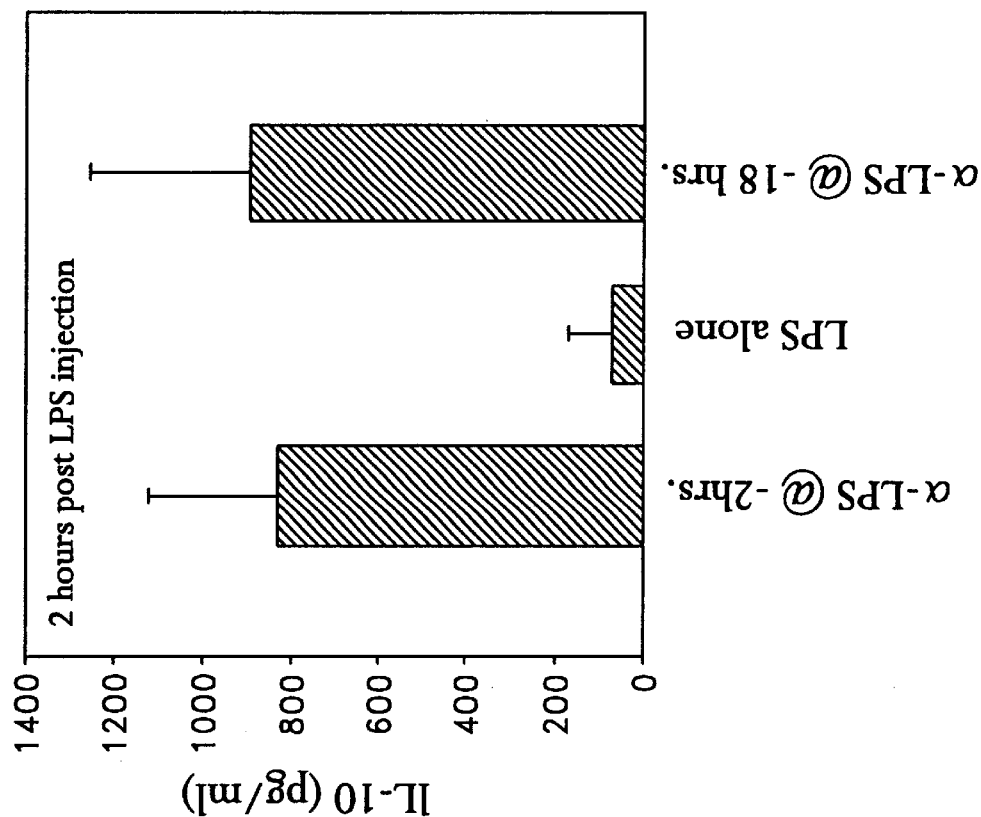
Figure 10A:
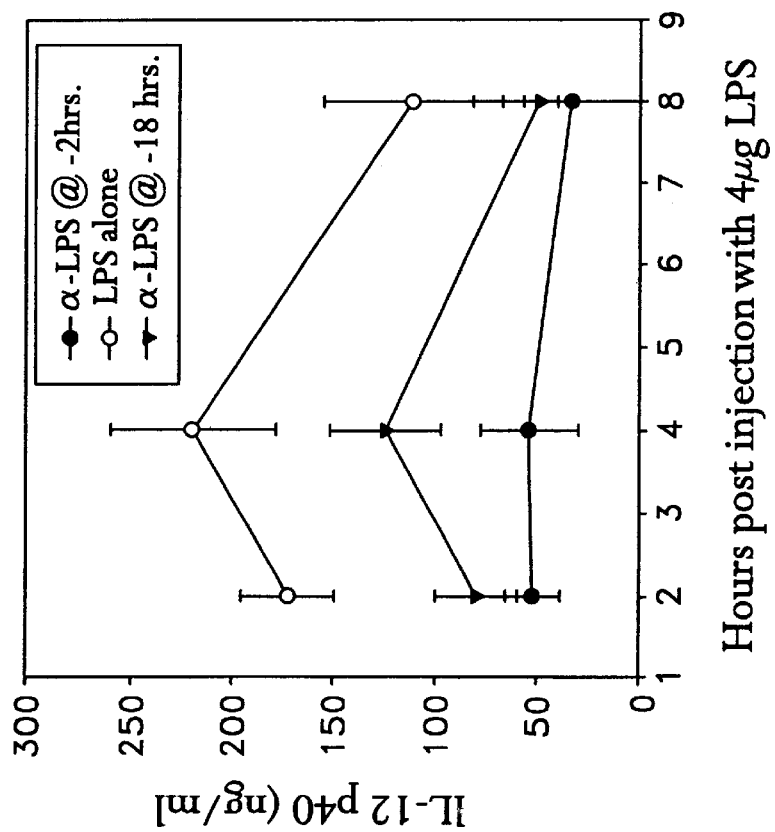

FIG. 10A is a plot IL-12(p40) serum levels in RAG-1$^{-/-}$ mice which received 100 μl of anti-LPS antibody intraperitoneally 2 or 18 hours before being injected intravenously with LPS (4 μg, *E. coli* 0128: B12). Control uninjected mice received LPS alone. Serum was collected at 2, 4, and 8 hours post LPS injection and assayed for IL-12(p40) production. Symbols in the figures represent mean serum cytokine levels from 5 mice±SD.

FIG. 10B is a graph of IL-10 serum levels in RAG-1$^{-/-}$ mice which received anti-LPS and/or LPS according to the same schedule of FIG. 10A. Serum was sampled two hours post LPS injection. Symbols in the figures represent mean serum cytokine levels from 5 mice±SD.

DETAILED DESCRIPTION OF THE INVENTION

Macrophages can respond to a variety of infectious and/or inflammatory stimuli by secreting an array of proinflammatory cytokines, such as IL-1, IL-6, IL-12 and TNFα. The overproduction of these proinflammatory cytokines, particularly IL-12, can result in shock or even death.

According to the present invention, ligation of the Fcγ receptor type I (FcγRI) on FcγRI-expressing cells such as macrophages leads to a selective upregulation of IL-10 production by those cells in response to proinflammatory signals. This upregulation occurs at the level of gene transcription and results in a increase in IL-10 protein secretion. The upregulation of IL-10 production is specific to FcγR1 ligation.

The human FcγRI receptor is a monomeric molecule having three Ig-like domains. The cDNAs for human and murine FcγRI have been identified by Allen and Seed, *Science* 243:378–80 (1989), and Sears et al., *J. Immunol.* 144:371–78 (1990), respectively, the entire disclosures of which are incorporated herein by reference.

The upregulation of IL-10 which results from FcγRI ligation occurs in cells exposed to a proinflammatory stimulus. By "proinflammatory stimulus" is meant an agent or condition, which acts on FcγRI-expressing cells such as macrophages to induce a proinflammatory response by those cells. Proinflammatory response is characterized by secretion of one or more proinflammatory molecules, such as TNFα, IL-1, IL-6 and IL-12. The proinflammatory stimulus which acts on macrophages to secrete these molecules typically comprises bacteria or components from bacterial cell walls, such as lipopolysaccharide (LPS). A macrophage or other FcγRI-expressing cell which has been acted upon by a proinflammatory stimulus is said to be "stimulated".

By "ligation" with respect to the FcγRI receptor on a cell is meant the formation of cross-links between a sufficient number of molecules of such receptor on the cell sufficient to stimulate IL-10 production by the cell.

By "ligating agent" is meant any substance which is capable of carrying out ligation of FcγRI receptors on cells.

By "enhance" or "enhancement" or "upregulation" with respect to the IL-10 production by FcγRI receptor-expressing cells is meant an increase in IL-10 production of at least two fold over the IL-10 production level of stimulated cells of the same type which are not exposed to ligating agent. Increases in IL-10 production of four fold, five fold and even as high as eight fold are possible.

It may be appreciated that any ligating agent must be at least bifunctional with respect to FcγRI binding in order to achieve cross-linking of the receptor, that is, a single molecule of ligating agent must be capable of simultaneously binding two or more receptors.

Ligation of FcγRI on FcγRI-expressing cells such as macrophages stimulates IL-10 production and leads to a marked suppression of IL-12 biosynthesis by IL-12 producing cells, particularly macrophages. Macrophage-derived IL-10 is a potent inhibitor of macrophage IL-12 production. Even IFNγ-primed macrophages fail to make IL-12 in response to LPS when exposed to macrophage supernatants containing IL-10. The ligation of the macrophage FcγRI downmodulates IL-12 production via a mechanism that is dependent on macrophage-derived IL-10.

The identification of the specific FcγR subtype, FcγRI, as the FcγRI receptor responsible for IL-10 upregulation, was determined in gene knockout mice. Macrophages from mice lacking the FcR γ chain, which is required for assembly and signaling by FcγRI and FcγRIII, failed to upregulate IL-10 in response to immune complexes. However, mice lacking either the FcγRII or the FcγRIII were fully capable of upregulating IL-10 production, thus establishing that FcγRI, and not FcγRII or FcγRIII, is the receptor responsible for IL-10, upregulation.

As further proof of the identification of the FcγRI receptor as the receptor responsible for IL-10 upregulation, FcγRI erythrocytes were opsonized with IgG3. IgG3 binds FcγRI exclusively, and does not bind FcγRII or FcγRIII (Gavinet al.,*J. Immunol* 160:20–23, 1998). The IgG3-opsonized erythrocytes were observed to enhance IL-10 production, confirming the role of FcγRI in this process.

The biological consequences of FcγRI ligation were determined in both in vitro and in vivo models of inflammation and sepsis. In all of the models tested the ligation of FcγR promoted the production of IL-10 and inhibited the secretion of IL-12. This reciprocal alteration in the pattern of macrophage cytokine production provides a useful therapeutic modality in suppressing macrophage proinflammatory responses.

According to the present invention, the FcγRI receptor is ligated by an agent which is capable of ligating that receptor. Preferably, the ligating agent binds specifically to the FcγRI, and does not also ligate the FcγRIII receptor, or ligates the FcγRIII receptor only minimally. The FcγRIII receptor is the prototypical proinflammatory Fc receptor. Ligating FcγRIII has been associated with the production of proinflammatory cytokines (Cassatella et al., *J. Exp. Med.* 169:549–567, 1989, and mice lacking FcγRIII undergo diminished Arthus reactions (Hazenbos et al., *Immunity* 5:181–188, 1996). Ligating the FcγRI receptor, without simultaneously ligating the FcγRIII receptor, provides enhancement of the anti-inflammatory response in treated individuals via upregulation of macrophage-derived IL-10 production without triggering the production of the proinflammatory cytokines associated with FcγRIII ligation. At the same time, the method of the present invention results in the suppression of the proinflammatory response through the potent inhibition of macrophage IL-12 production by macrophage-derived IL-10.

While a mechanism whereby receptor ligation can downmodulate IL-12 production by macrophages was previously described by Sutterwala et al., *J. Exp. Med.* 185:1977–1985 (1997), that mechanism of IL-12 downregulation did not exhibit specificity with regard to the macrophage phagocytic receptors that induced the downmodulation. Moreover, the IL-12 downregulation following receptor ligation described by Sutterwala et al. was transient, $Ca^{++}$ dependent and IL-10 independent.

The present invention arises from a novel mechanism of IL-12 downregulation which is distinct from the previously described mechanisms in several important ways. The present mechanism does not involve a direct regulation of IL-12 transcription, but rather depends on the production of the inhibitory cytokine IL-10, which acts on IL-12-producing cells. The IL-12 downregulation mediated by IL-10 is not $Ca^{++}$-dependent, and has a markedly longer duration than the transient downregulation of IL-12 observed by Sutterwala et al. Moreover, the IL-10-mediated IL-12 downregulation of the present invention is specific to a single receptor class on macrophages, the FcγRI.

FcγRII has been shown to be a negative regulator of immune complex-triggered immune responses, and mice lacking FcγRII have augmented anaphylactic responses to IgG (Takai et al.,*Nature* 379:346–349 (1996)). However, FcγRI operates via a different mechanism than that observed for FcγRII. Whereas FcγRII inhibits signaling through the FcγR (Muta et al, *Nature* 368:70–73, 1994), FcγRI actively promotes the transcription of an inhibitory cytokine, IL-10. Thus, although both FcγRI and FcγRII can mediate inhibition of inflammatory responses to immune complexes, they do so by two distinct mechanisms.

Preferably, the ligating agent of the present invention is completely specific for the FcγRI receptor and does not induce ligation of either FcγRII or FcγRIII.

Ligating agents for FcγRI may be identified by a screening assay utilizing appropriate test cells as reagents. Fibroblasts or eptheliod cells, which do not express FcγRI, are transfected with FcγRI cDNA to express FcγRI. Transfection may be carried out utilizing the procedure described by Sutterwala et al., *J. Leukocyte Biol.* 59:883 (1996) (incorporated herein by reference) for obtaining stable cell surface expression of complement receptor type I (CR 1) and complement receptor type 3 (CR3) in Chinese hamster ovary (CHO) cells. Briefly, cells are cotransfected with pRSVneo and a plasmid containing the complete cDNA of the human FcγRI receptor (Allen and Seed, *Science* 243:378–80, 1989) (incorporated herein by reference) cloned into the $Ap^pM8$ expression vector. Transfected cells are selected in medium containing G418 sulfate. The cell surface expression of FcγRI is confirmed by flow cytometry, according to known techniques. As a negative control screening reagent, transfectants expressing the human FcγRIII are prepared according to the same procedure.

One of two assays may be employed in utilizing the transfectants to detect ligating agents that specifically bind to the human FcγRI, According to a direct binding assay, the candidate ligating agent is labeled with fluorescein isothiocyanate (FITC) according to standard techniques. FITC-labeled ligating agent is then added to parallel wells of transfected cells expressing either the FcγRI or the FcγRIII for thirty minutes at 4° C. The cells are washed and then fixed in 4% paraformaldehyde and analyzed by flow cytometry. Agents which bind to the FcγRI-expressing cells, but not the FcγRIII-expressing cells, are selected.

According to a competitive binding assay, candidate ligating agent is examined for ability to compete with a known labeled FcγRI-binding agent for binding to FcγRI. This assay is used where the direct binding assay is not conveniently employed, such as where the candidate ligating agent is not easily labeled. This is true for small synthetic molecules, for example.

According to the competitive binding assay, unlabeled candidate ligating agent is added to FcγRI-transfected cells at 4° C. for 30 minutes. Following this incubation, FITC-labeled human IgG1, which binds specifically to human FcγRI, is added for an additional 30 minutes at 4° C. After washing, the cells are fixed in paraformaldehyde and processed for flow cytometry. Control cells which have not been exposed to ligating agent will bind FITC-labeled IgG1 and fluoresce. Cells which bind ligating agent via the FcγRI will exhibit decreased fluorescence. Reagents testing positive as ligating agents for FcγRI will yield a decreased fluorescence.

Ligation of the FcγRI receptor may be accomplished by contacting the cells with a ligating agent for the receptor. According to one embodiment of the invention, the ligating agent comprises an IgG immune complex which is capable of cross-linking the FcγRI receptor. By "immune complex" is meant a macromolecular complex comprising IgG antibody molecules bound together by antigen. The IgG antibody in the immune complex may be polyclonal or monoclonal. Such cross-linking immune complexes contain at least two IgG. antibody molecules, or at least two fragments of IgG antibody molecules which maintain ability to be bound by the FcγRI receptor. Antibody fragments are typically generated by treatment of antibodies with an enzyme such as papain or pepsin. Such antibody fragmentation methods are well-known to those skilled in the art. The antibody of the immune complex may comprise one or more antibody fragments which maintain the ability to form immune complexes, i.e., bind antigen, and which maintain the ability to be bound and be bound by the FcγRI receptor. Thus, the antigen binding sites on the antibody must be preserved to the extent necessary to bind antigen, and the Fc segment of the antibody must be preserved to the extent necessary to comprise a specific recognition site for the FcγRI receptor.

It may be appreciated that the antibody of the immune complex may comprise a monovalent antibody or antibody fragment, in addition to or in lieu of multivalent antibodies and antibody fragments. By "multivalent" is meant antibody which is at least divalent, that is, has at least two antigen binding sites. This is because the spanning of neighboring FcγRI receptors on macrophages by immune complex ligating agents occurs by receptor binding to the antibody Fc region. So long as the immune complex contains at least two such antibody molecules and thus at least two Fc segments available for binding to FcγRI neighboring FcγRI receptors on the cell, cross-linking of those receptors will occur, thereby inducing stimulation of IL-10 secretion by the cell.

Preferably, the immune complex comprises an protein-antibody complex or a polysaccharide-antibody complex. The antigen should not be toxic to the host. The antigen should be sufficiently small in size so as not to induce immune complex disease, such as glomerulonephritis. Preferably, the antigen consists of a peptide derived from a nontoxic protein such as albumin, combined with antibodies which react with specific portions of the peptide. Alternatively, a synthetic saccharide complexed with human IgG2, for example, may be utilized as the immune complex.

According to another embodiment of the invention, the ligating agent comprises an IgG multimer capable of cross-linking the FcγRI receptor. By "multimer" is meant an association of two or more IgG antibody molecules, or two or more IgG fragments containing the Fc region. The multimer thus contains two or more antibody Fc regions.

Antibodies can be induced to form multimers according to well-known techniques. Dimeric IgG or trimeric IgG is preferred, or a mixture thereof. Dimers and trimers are preferred because of the adverse side effects associated with formation of higher multimers, which may result in the formation of large complexes or "aggregates". IgG aggregates may cause the release of anaphylatoxins into the bloodstream via complement activation. Glomerulonephritis is also known to result when large immune complexes form in the kidneys. Human IgG for this purpose may be obtained in large quantities from pooled blood or outdated plasma. IgG preparations for intravenous administration are commercially available. The use of pooled human IgG is possible because the antigenic specificity of the IgG is irrelevant for purposes of this embodiment of the invention.

The antibodies comprising the IgG multimers may comprise monoclonal or polyclonal antibodies, and may comprise whole antibody molecules or fragments thereof which maintain the ability to be bound by the FcγRI receptor.

IgG dimers and trimers are formed by allowing formation of multimeric forms of IgG of various sizes, followed by selection of dimers and trimers by size exclusion chromatography, using standard chromatographic techniques. IgG multimers are spontaneously generated by combining IgG monomer from different individuals. IgG dimers are prevalent in Ig prepared from pooled plasma, whereas Ig prepared from single-donor plasma is virtually monomeric.

IgG preparations containing multimers are prepared according to well-known techniques, beginning with pooled plasma. Therapeutic immunoglobulins are prepared from large pools of human plasma by the Cohn-Oncley process, which relies on selective precipitation with ethanol at subzero temperatures (Cohn et al., *J. Am. Chem. Soc.* 68, 459 (1946); Oncley et al., *J. Am. Chem. Soc.* 71, 541 (1949) According to the methodology of Kistler and Nitschmann, *Vox Sang.* 7, 414 (1962), proteins present in plasma, including immunoglobulins, may be selectively precipitated through manipulation of pH, protein concentration, alcohol concentration, ionic strength and temperature. Fraction II of the Cohn-Onclay process (fraction GC of the Kistler-Nitschmann scheme) consists of essentially pure IgG, with only trace amounts of other plasma proteins such as IgA or IgM.

Contrary to prior methods for forming intramuscular and intravenous Ig, which seek to avoid formation of IgG dimers, the composition of the therapeutic IgG preparation of the present invention is manipulated to select for IgG dimers and trimers, over monomers. Factors which facilitate dimer formation are discussed by Tankersley, *Immunological Reviews* 139:159–72 (1994), the entire disclosure of which is incorporated herein by reference. The exposure of monomeric IgG to oxygen radicals causes aggregate formation (Kleinveld et al., *Scand. J. Rheumatology* S75:157–163 (1988) (incorporated herein by reference). Thus, exposure of a solution of IgG to UV light can be used to favor multimer formation.

IgG multimers, preferably IgG dimers, may also be generated by cold-induced polymerization of IgG monomers, as described by Vialtel et al., *J. Biol. Chem.* 257:3811–3818 (1982), the entire disclosure of which is incorporated herein by reference. IgG is cooled, and then dimers and trimers are separated from monomers and aggregates by size exclusion chromatography.

IgG dimers and trimers may be selected from IgG multimer mixtures according to standard chromatographic techniques, such as described by Lee et al., *J. Chromatography* 444:141–52 (1988), the entire disclosure of which is incorporated herein by reference. For example, separation of IgG monomer, dimer and aggregate components from an IgG mixture may be achieved at ambient temperature by isocratic elution with a mobile phase consisting of 0.2 M dibasic potassium phosphate (pH 7.0) containing 0.02% sodium azide. A typical run time is 40 minutes, using the following size-exclusion chromatography system: two Beckman Spherogel™ TSK 3000 SW columns connected in series (60 cm×7.5 mm combined length), a Waters Model 6000 A pump (set at 00.5 ml/min.), a Waters Model 440 absorbance detector (set at 280 nm and 0.5 a.u.f.s.), a Waters WISP Model 710B autoinjector (set at 200-$\mu$l injections), and a Houston Instruments Omniscribe recorder (set at 0.1 inches/min.). IgG aggregate, dimer, and monomer peaks are eluted at retention times of 18.2, 21.6, and 25.8 minutes, respectively.

While IgG preparations have been available for human therapeutic use, such preparations predominately comprise IgG monomer. For utilization in the practice of the present invention, such preparations are first enriched for dimers and/or trimers. At least about 50%, preferably at least about 80%, more preferably at least about 90%, most preferably about 95%, of the IgG content of the preparation, by weight, should comprise IgG dimer, trimer or combination thereof. IgG dimers are preferred over IgG trimers.

IgG dimers and trimers may also be formed by chemically cross-linking IgG monomers with covalent cross-linking agents. One such agent is the bifunctional cross-linker dithiobis(succinimidylpropriionate) ("DSP"). IgG may be cross-linked in this fashion according to the method of Wright al, *Biochem. J.* 187:767–774 (1980), and 187:775–780 (1980), the entire disclosures of which are incorporated herein by reference. Other commercially available cross-linking agents (for example from Pierce Chemical Company, Rockford, Ill.) may be substituted for DSP. Such cross-linking agent include the cross-linking agents identified below.

According to another embodiment of the invention, the ligating agent comprises an Fc fragment multimer comprising two or more Fc fragments which are coupled together. Preferably, the fragments are joined by a linking group forming a covalent bond. Covalently cross-linked Fc fragment dimers may be prepared by utilizing homobifunctional cross-linking reagents, e.g., disuccinimidyl tartrate, disuccinimidyl suberate, ethylene glycolbis(succinimidyl succinate), 1,5-difluoro-2,4-dinitrobenzene ("DFNB"), 4,4'-diisothiocyano-2,2'-disulfonic acid stilbene ("DIDS"), and bismaleimidohexane ("BMH").

Alternatively, heterobifunctional cross-linking reagents may be employed. Such agents include, for example, N-succinimidyl-3-(2-pyridyldithio)propionate ("SPDP"), sulfosuccinimidyl-2-(p-azidosalicylamido)ethyl-1-3'-dithiopropionate ("SASD", Pierce Chemical Company, Rockford, Ill.), N-maleimidobenzoyl-N-hydroxy-succinimidyl ester ("MBS"), m-maleimidobenzoylsulfosuccinimide ester ("sulfo-MBS"), N-succinimidyl(4-iodoacetyl)aminobenzoate ("SIAB"), succinimidyl 4-(N-maleimidomethyl)-cyclohexane-1-carboxylate ("SMCC"), succinimidyl-4-(p-maleimidophenyl)butyrate ("SMPB"), sulfosuccinimidyl(4-iodoacetyl)aminobenzoate ("sulfo-SIAB"), sulfosuccinimidyl 4-(N-maleimidomethyl)cyclohexane-1-carboxylate("sulfo-SMCC"), sulfosuccinimidyl 4-(p-maleimidophenyl)-butyrate ("sulfo-SMPB"), bromoacetyl-p-aminobenzoyl-N-hydroxy-succinimidyl ester, iodoacetyl-N-hydroxysuccinimidyl ester, and the like.

For heterobifunctional cross-linking, a Fc fragment is derivatized with, e.g., the N-hydroxysuccinimidyl portion of the bifunctional reagent, and the derivatized Fc fragment is purified by gel filtration. Next, a second Fc fragment is reacted with the second functional group of the bifunctional reagent, assuring a directed sequence of binding between components of the Fc dimer.

Typical heterobifunctional cross-linking agents for forming protein-protein conjugates have an amino-reactive N-hydroxysuccinimide ester (NHS-ester) as one functional group and a sulfhydryl reactive group as the other functional group. First, epsilon-amino groups of surface lysine residues of the first Fc fragment are acylated with the NHS-ester group of the cross-linking agent. The second Fc fragment, possessing free sulfhydryl groups, is reacted with the sulfhydryl reactive group of the cross-linking agent to form a covalently cross-linked dimer. Common thiol reactive groups include maleimides, pyridyl disulfides, and active halogens. For example, MBS contains a NHS-ester as the amino reactive group, and a maleimide moiety as the sulfhydryl reactive group.

Photoactive heterobifunctional cross-linking reagents, e.g., photoreactive phenyl azides, may also be employed. One such reagent, SASD, may be linked to an Fc fragment via its NHS-ester group.

As an alternative to intact IgG, or multimers comprising native IgG Fc fragments, the ligating agent may comprise either synthetic or recombinant peptides which comprise the Fc region. For example, a single recombinant peptide may be designed comprising two Fc regions joined by an appropriate spacer segment.

According to another embodiment of the invention, the ligating agent comprises a multivalent antibody against the FcγRI receptor. The antibody may be directed against any determinant on the FcγRI receptor. Preferably, the determinant is unique to the FcγRI receptor, and not shared by FcγRII or FcγRIII. The multivalent antibody may be monoclonal or polyclonal. The antibody may comprise intact antibody, or fragments capable of binding antigen, providing the fragments are divalent, e.g., F(ab')$_2$ and Facb fragments. For use as ligating agents in human subjects, such antibodies would be of animal origin, but would be preferably "humanized". Humanized murine antibodies have been prepared in which only the minimum necessary parts of the mouse antibody, the complementarity-determining regions (CDRs), are combined with human V region frameworks and human C regions (Jones et al. Nature 321, 522–525, 1986; Verhoeyen et al., Science 239, 1534–1536, 1988; Reichmann et al., 322, 323–327, 1988; Hale et al., Lancet 2, 1394–1399, 1988; Queen et al., Proc. Natl. Acad. Sci. USA 86,10029–10033, 1989). The entire disclosures of the aforementioned papers are incorporated herein by reference. This technique results in the reduction of the xenogeneic elements in the humanized antibody to a minimum. Rodent antigen binding sites are built directly into human antibodies by transplanting only the antigen binding site, rather than the entire variable domain, from a rodent antibody. This technique is available for production of chimeric rodent/human anti-FcγRI antibodies of reduced human immunogenicity.

The ligating may be administered to patients in circumstances where it is desired to obtain a therapeutic anti-inflammatory effect, or to inhibit or prevent an undesired IL-12-mediated proinflammatory response.

As an alternative to administering an exogenous ligating agent, it is possible to form the ligating agent in situ in the body of the patient, by administering antibody to a target antigen. Upon uptake by the body, the antibody combines with its target antigen to form an immune complex including the target antigen. Such in situ-formed immune complexes comprising two or more IgG antibodies function as a ligating agents to ligate FcγRI receptors on macrophages to induce IL-10, and in turn inhibit IL-12, production.

The target antigen for achieving formation of immune complexes in vivo is selected according to the etiology of the disease. The specificity of the therapeutic antibody is designed accordingly. For example, an immune response to DNA and chromatin is frequently observed in autoimmune diseases such as systemic lupus erythematosus (SLE). IgG antibody specific for DNA or chromatin may be administered to such individuals. The antibody will form a complex only when the autoimmune antigen is present, i.e., only during episodes of autoimmune flare-up. Thus, IgG may be administered as an anti-inflammatory agent which would be functional only when needed, that is, when the autoimmune antigen is expressed. Antibody that does not form complexes with the autoimmune antigen is cleared from the circulation according to the half-life of the immunoglobulin. The antibodies are preferably humanized to reduce their antigenicity and to increase their half-life in plasma.

The present invention thus provides a treatment for autoimmune disorders including moderately acute autoimmune disorders such as Kawasaki Disease; and chronic autoimmune disorders such as SLE, rheumatoid arthritis, inflammatory bowel disease, Sydenham's chorea (post Streptococcal), and autoimmune hemolytic anemia. For treatment of autoimmune disorders, ligating agent according to the present invention is administered, preferably parenterally, most preferably intravenously.

The ligating agent may be administered as a treatment for conditions having a proinflammatory component, such as enteric bacterial infections which produce the pharmacologically active lipopolysaccharide endotoxin from the bacterial cell wall, known as endotoxin or LPS. Endotoxin from a wide variety of unrelated bacterial species behave quite similarly, regardless of the inherent pathogenicity of the microorganism from which they are derived or their antigenic structure. In particular, the method of the present invention is useful for treating the endotoxemia or septic shock which arises from bacteremia caused by gram-negative bacilli.

Bacteremia arises from blood system invasion by enteric bacteria, most commonly from urinary tract infection, post surgical disease of the gastrointestinal tract (e.g., following bowel surgery), infections developing at the site of "cutdowns" and intravenous catheters, postpartum or postabortal sepsis, and infection of wounds, ulcer, burns, and internal prosthetic devices. Shock attributed to endotoxemia is due to the release of the proinflammatory cytokines IL-1, IL-6, IL-12 and TNFα, most particularly IL-12. Stimulation of IL-10 secretion by exogenously administered or in vivo-formed ligating agent can lead to the rapid downregulation of proinflammatory cytokine release, and the prevention or abatement of shock symptoms.

According to another embodiment for treating endotoxemia, the treatment is carried out by administering an appropriate antibody which leads to the in vivo formation of ligating agent. For this purpose, the antibody is preferably directed against bacterial endotoxin, leading to the in vivo formation of IgG-endotoxin complexes. These immune complexes are effective in ligating FcγRI receptors on macrophages participating in the proinflammatory response to the endotoxin. Of course, efforts should be undertaken to also treat the underlying enteric bacterial infection, such as described by Kunin in "Enteric Bacterial Infections", in *Textbook of Medicine*, P. Beeeson et al. eds., 15th edition, W. B. Saunders Co., Philadelphia, Pa., 1979, p.453–457.

The ligating agent (or antibody to induce in vivo formation of ligating agent) may be administered by any method which achieves an adequate distribution of the ligating agent in the target tissue. The ligating agent or antibody is preferably administered parenterally, most preferably intravenously or intraarterially. The administration may take the form of one or more injections or continuous or semi-continuous infusions. For the treatment of septic shock, a single bolus injection is contemplated. For the treatment of immune disorders, one or more injections are utilized, as needed. For a ligating agent comprising IgG dimers, for example, a representative dosage may range from about 0.05 to about 1.0 g/kg, more preferably from about 0.1 to about 0.5 g/kg. For administration of IgG to achieve in situ formation of therapeutic immune complexes against target antigens such as LPS, the dosage may range from about 0.1 to about 20 mg/kg, preferably from about 1 to about 10 mg/kg.

The ligating agent (or antibody) is advantageously formulated by combination with a pharmaceutically acceptable carrier suitable for administration of antibodies. For intravenous administration, the ligating agent or antibody is contained in a preservative-free sterile saline solution, for example. One or more additives, such as stabilizers and additives for inhibiting the formation of antibody aggregates, may be also be included in the preparation. Representative anti-aggregating agents including polysorbate 80 and tri-n-butyl phosphate. One representative formulation for intravenous administration of antibody comprises D-sorbitol (50 mg/ml), human albumin (1 mg/ml), polyethylene glycol (100 mcg), polysorbate 80 (100 mcg) and tri-n-butyl phosphate.

The practice of the invention is illustrated by the following non-limiting examples.

EXAMPLE 1

Effect of FcγR Ligation on Mouse Macrophage IL-10 Production

The production of IL-10 by bone marrow-derived macrophages (BMMΦ) was examined following specific FcγR ligation as follows. The ligating agent comprised IgG-opsonized sheep erythrocytes.

A. Macrophages

Six- to eight-week-old BALB/c and C57BL/6 mice were obtained from Taconic (Germantown, N.Y.). Bone marrow-derived macrophages (BMMΦ) were established as previously described (Sutterwala et al., *J. Exp. Med.* 185:1977–1985, 1997). Briefly, bone marrow cells were differentiated in DMEM containing 20% L929 cell-conditioned medium, 10% heat-inactivated (HI)-FCS, 2 mM L-glutamine, 100 U/ml penicillin G, and 100 μg/ml streptomycin for 5 to 7 days until uniform monolayers of macrophages were established. Twelve hours before use, cells were removed from the original plastic petri dishes by EDTA and were plated in tissue culture-treated six- or twenty four-well plates (Nunc, Naperville, Ill.) in DMEM containing 10% HI-FCS, 2 mM L-glutamine, 100 U/ml penicillin G, and 100 μg/ml streptomycin (complete medium).

B. Opsonized Erythrocytes

IgG-opsonized sheep erythrocytes (E-IgG) were generated by incubating SRBC (Lampire, Pipersville, Pa.) with rabbit anti-SRBC IgG (Cappel, Durham, N.C.) at nonagglutinating titers for 40 minutes at room temperature. E-IgG were washed and resuspended in HBSS (GIBCO BRL, Grand Island, N.Y.) prior to their addition to macrophages. Complement-opsonized erythrocytes (E-C3bi) were generated by incubating SRBC with culture supernatants of hybridoma S-S.3 (anti-SRBC IgM/κ[ATCC, Rockville, Md.]) at nonagglutinating titers for 40 minutes at room temperature. IgM-opsonized erythrocytes were washed twice with HBSS and resuspended at $1\times10^8$ cells/ml in HBSS with 10% murine C5-deficient serum. Following a 15-minute incubation at 37° C., E-C3bi were washed and resuspended in HBSS prior to their addition to macrophages. Erythrocytes were added to macrophage monolayers at a ratio of 20:1.

C. Macrophage Stimulation

Monolayers of the BMMΦ were washed once with complete medium, and then stimulated with LPS (*Escherichia coli* 0127:B8 [Sigma, St. Louis, Mo.]) at a final concentration of 100 ng/ml, in the presence or absence of opsonized erythrocytes (E-IgG or E-C3bi).

D. Competitive Quantitative RT-PCR

Six hours following the addition of stimuli, total RNA was extracted from $10^6$ BMMΦ using RNAzol B according to the manufacturer's instructions. RNA was reverse transcribed using Superscript II RT (GIBCO BRL) and random hexamer primers (Promega, Madison, Wis.). PCR was performed using a multiple cytokine-containing competitor PQRS, as previously described (Reiner et al, *J. Immunol. Methods* 165:37–46, 1993) and a fixed concentration of competitor in each reaction.

Figure 1A:
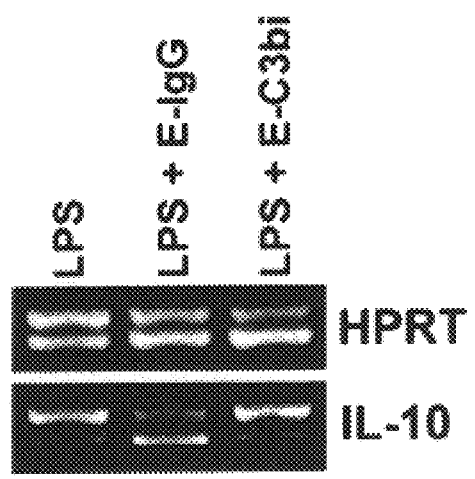
FIG. 1A shows the competitive quantitative reverse transcription-polymerase chain reaction (RT-PCR) analysis of IL-10 production in murine bone marrow-derived macrophages (BMMΦ) exposed to LPS alone or LPS in combination with either IgG-opsonized sheep erythrocytes (E-IgG) or complement-opsonized sheep erythrocytes (E-C3bi). Concentrations of input cDNAs were first adjusted, using the housekeeping gene hypoxanthine-guanine phosphoribosyltransferase (HPRT), to yield comparable ratios of competitor (upper band in each reaction in top panel of FIG. 1A) to wild-type (lower band in each reaction in top panel of FIG. 1A) intensities for the amplification reaction for HPRT. The adjusted input cDNAs were then used in subsequent RT-PCR reactions using primers for IL-10 (bottom panel in FIG. 1A).

In brief, concentrations of input cDNAs were first adjusted using the housekeeping gene hypoxanthine-guanine phosphoribosyltransferase (HPRT). Input cDNAs were adjusted to yield comparable ratios of competitor (FIG. 1A, upper band in each reaction) to wild-type (FIG. 1A, lower band in each reaction) intensities for the amplification reaction for HPRT. Amplification products were resolved on 2.0% ethidium-stained agarose gels. The results are set forth in FIG. 1A. The larger molecular weight competitor bands provide an internal standard for the relative amounts of the lower molecular weight experimental cDNAs.

Figure 1B:
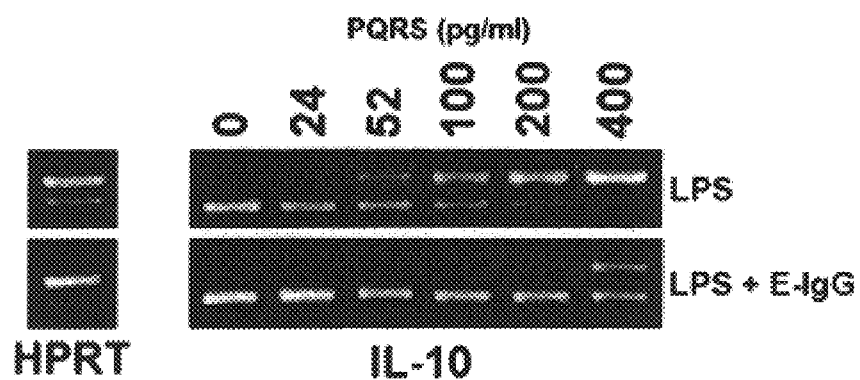
FIG. 1B shows the competitive quantitative RT-PCR analysis of IL-10 production in murine BMMΦ exposed to LPS alone or LPS in combination with E-IgG, following normalization for HPRT levels. Constant volumes of normalized cDNAs were amplified in the presence of increasing concentration of the multiple cytokine-containing competitor PQRS, using primers for IL-10.

Constant volumes of normalized cDNAs were then amplified in the presence of decreasing concentrations of competitor (PQRS), using primers for IL-10 (Sutterwala et al.,*J. Exp. Med.* 185:1977–1985, 1997). The results are shown in FIG. 1B. The concentration of the experimental cDNA is represented by the equivalent intensities of competitor and wild-type bands. The fold increase in IL-10 levels between BMMΦ exposed to LPS or LPS in combination with E-IgG can be determined by taking the ratio of their equivalence points. IL-10 mRNA was increased by 4 to 8-fold.

E. Cytokine ELISA

Figure 2:
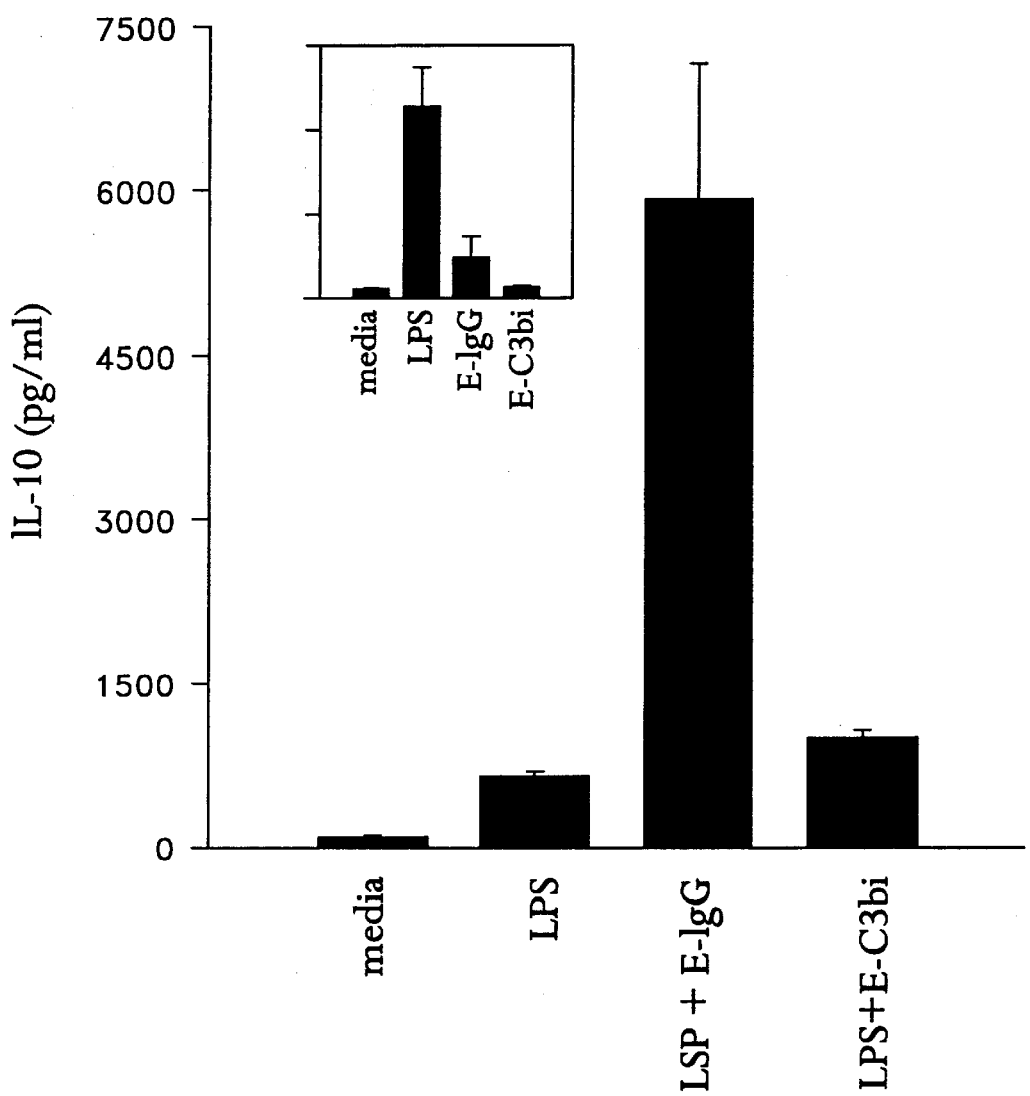
FIG. 2 is a graph of the enzyme-linked immunosorbent assay (ELISA) determination of IL-10 in supernatants of murine BMMΦ exposed to either media, LPS, E-IgG, or E-C3bi (inset), or LPS alone or LPS in combination with either E-IgG or E-C3bi.

Cytokines levels in BMMΦ supernatants were measured by enzyme-linked immunosorbent assay (ELISA) 24 hours following the addition of stimuli using appropriately diluted cell supernatants. IL-10 concentrations were determined with a mouse IL-10 ELISA kit (Genzyme Corp., Cambridge, Mass. or Biosource International, Camarillo, Calif.) according to the manufacturer's instructions. The results are shown in FIG. 2. The inset in FIG. 2 results from BMMΦ exposed to either media, LPS or erythrocytes opsonized with IgG (E-IgG) or C3bi (E-C3bi). The main body of FIG. 2 results from exposure of BMMΦ to LPS alone or LPS in combination with either E-IgG or E-C3bi. Values in FIG. 2 represent the mean of three independent experiments, each performed in triplicate, ±SE.

F. Discussion of Results

The addition of LPS to monolayers of BMMΦ induced a modest but significant production of IL-10 by macrophages (FIG. 1), as previously reported (de Waal et al., *J. Exp. Med.* 174:1209–2120, 1991). The ligation of FcγR simultaneously with the addition of LPS, however, markedly enhanced the production of IL-10. This enhancement was observed at both the mRNA (FIG. 1A) and protein (FIG. 2) levels. IL-10 mRNA was increased by 4 to 8-fold (FIG. 1B), and protein secretion was increased by greater than 6-fold following FcγR ligation (FIG. 2). The induction of IL-10 was specific to the FcγR because ligation of macrophage complement receptors did not significantly alter IL-10 mRNA (FIG. 1A) or protein (FIG. 2) production.

Macrophage complement and FcγR were also ligated in the absence of LPS to determine whether receptor ligation alone was sufficient to trigger IL-10 production (FIG. 2 inset). The ligation of neither of these receptors was sufficient to induce the production of significant levels of IL-10. Thus, FcγR ligation on unstimulated macrophages is not sufficient to trigger the production of IL-10.

EXAMPLE 2

Effect of FcγR Ligation on Macrophage IL-10 Production by Gene Knockout Mice

In order to determine the FcγR subtype responsible for IL-10, upregulation, bone marrow derived macrophages (BMMΦ) from gene knockout mice were studied. The FcR γ chain is an essential component of both the FcγRI and the FcγRIII, and is required for both receptor assemble and signaling (Takai et al., *Cell* 76:519–529, 1994).

A. Macrophages

BMMΦ were derived according to the preparative procedure of Example 1 from each of the following mice: (i) FcR γ chain-deficient (FcRγ$^{-/-}$) (Takai et al., *Cell* 76:519–529, 1994); (ii) FcγRII-deficient (FcRIIγ$^{-/-}$) (Takai et al., *Nature* 379:346–349, 1996); (iii) FcγRIII-deficient (FcRIIIγ$^{-/-}$) (Hazenbos et al., *Immunity* 5:181–188, 1996); (iv) normal C57BL/6 mice.

B. Macrophage Stimulation and IL-10 ELISA

BMMΦ were exposed to LPS alone or LPS in combination with either E-IgG or unopsonized erythrocytes (E), as in Example 1. After 24 hours the supernatant was harvested and IL-10 levels were determined by ELISA as above. Determinations were performed in triplicate, and values are expressed as the means±SD. The results, set forth in FIG. 2, are representative of three separate experiments.

C. Discussion of Results

Figures 3A, 3B:
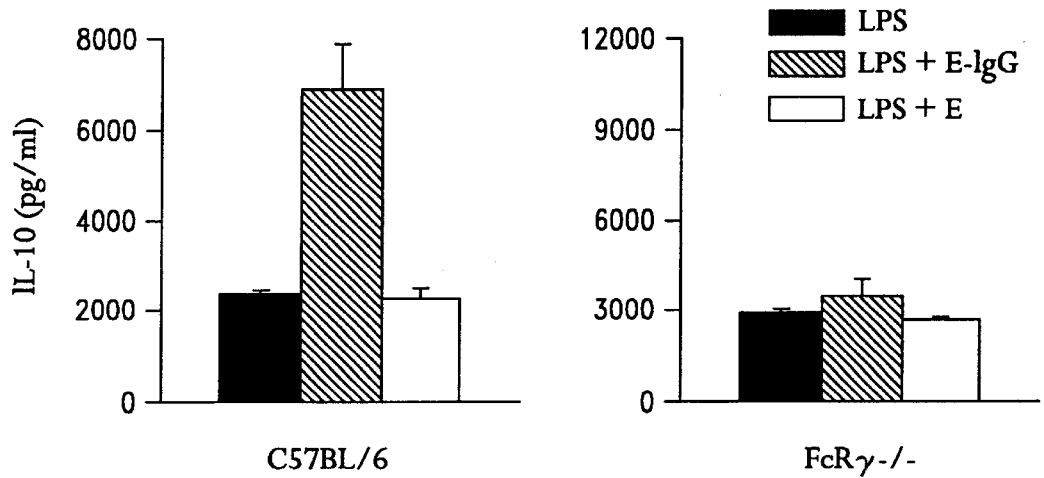
FIGS. 3A through 3D comprise graphs of ELISA determinations of IL-10 in supernatants of BMMΦ of various mouse strains exposed to LPS alone or LPS in combination with either E-IgG or unopsonized erythrocytes (E): 3A, C57BL/6; 3B, FcRγ$^{-/-}$; 3C, FcγRII$^{-/-}$; 3D, FcγRIII$^{-/-}$.
Figures 3C, 3D:
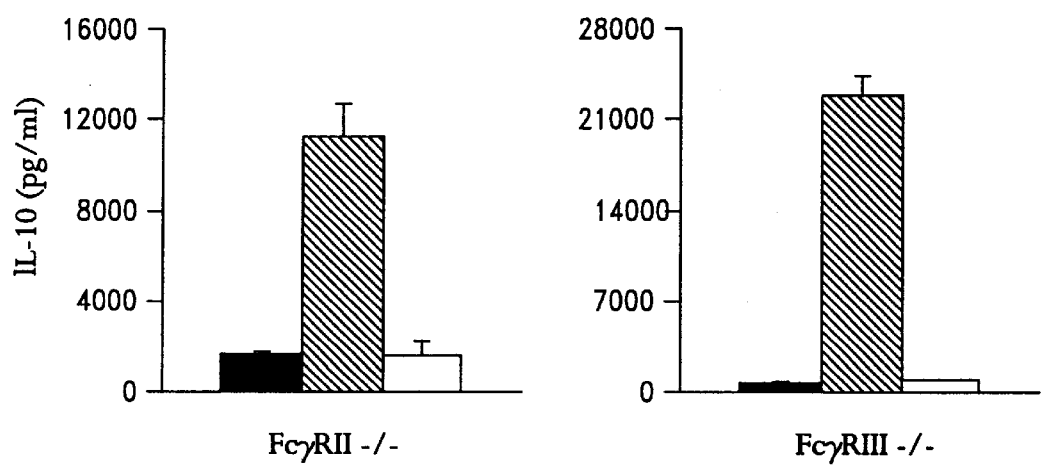

The FcR γ chain is an essential component of both the FcγRI and the FcγRIII, and is required for both receptor assembly and signaling (Takai et al., *Cell* 76:519–529, 1994). Macrophages from mice lacking the common γ chain (FcRγ$^{-/-}$) failed to upregulate IL-10 production (FIG. 3B), implicating one of these two receptors in this phenomenon. Macrophages derived from normal mice (FIG. 3A), mice lacking FcγRII (FIG. 3B), and mice lacking FcγRIII (FIG. 3C) were fully capable of upregulating IL-10 production in response to E-IgG. These results are consistent with the high affinity FcγRI being the mediator of IL-10 induction.

EXAMPLE 3

Effect of Specific FcγRI Ligation on Mouse Macrophage IL-10 Production

To directly demonstrate the role of FcγRI in the upregulation of IL-10 biosynthesis, erythrocytes were opsonized with IgG3 (E-IgG3), a subclass of antibody that binds exclusively to FcγRI (Gavin et al., *J. Immunol.* 160:20–23, 1998).

A. IgG3-Opsonized Erythrocytes

To specifically opsonize sheep erythrocytes with IgG3, the erythrocytes were incubated with a 1:10 dilution of ascitic fluid containing the mAb N-S.7 (anti-SRBC IgG3). The N-S.7 hybridoma was obtained from the ATCC (Rockville, Md.).

B. Macrophage Stimulation and IL-10 ELISA

BMMΦ were exposed to either media, E-IgG3, unopsonized erythrocytes (E) or LPS alone or LPS in combination with either E-IgG3 or E, according to the procedure of Example 1. After 24 hours the supernatant was harvested and IL-10 levels were determined by ELISA as above. Determinations were performed in triplicate, and values are expressed as the means±SD. The results, set forth in FIG. 4, are representative of two separate experiments.

C. Results

Figure 4:
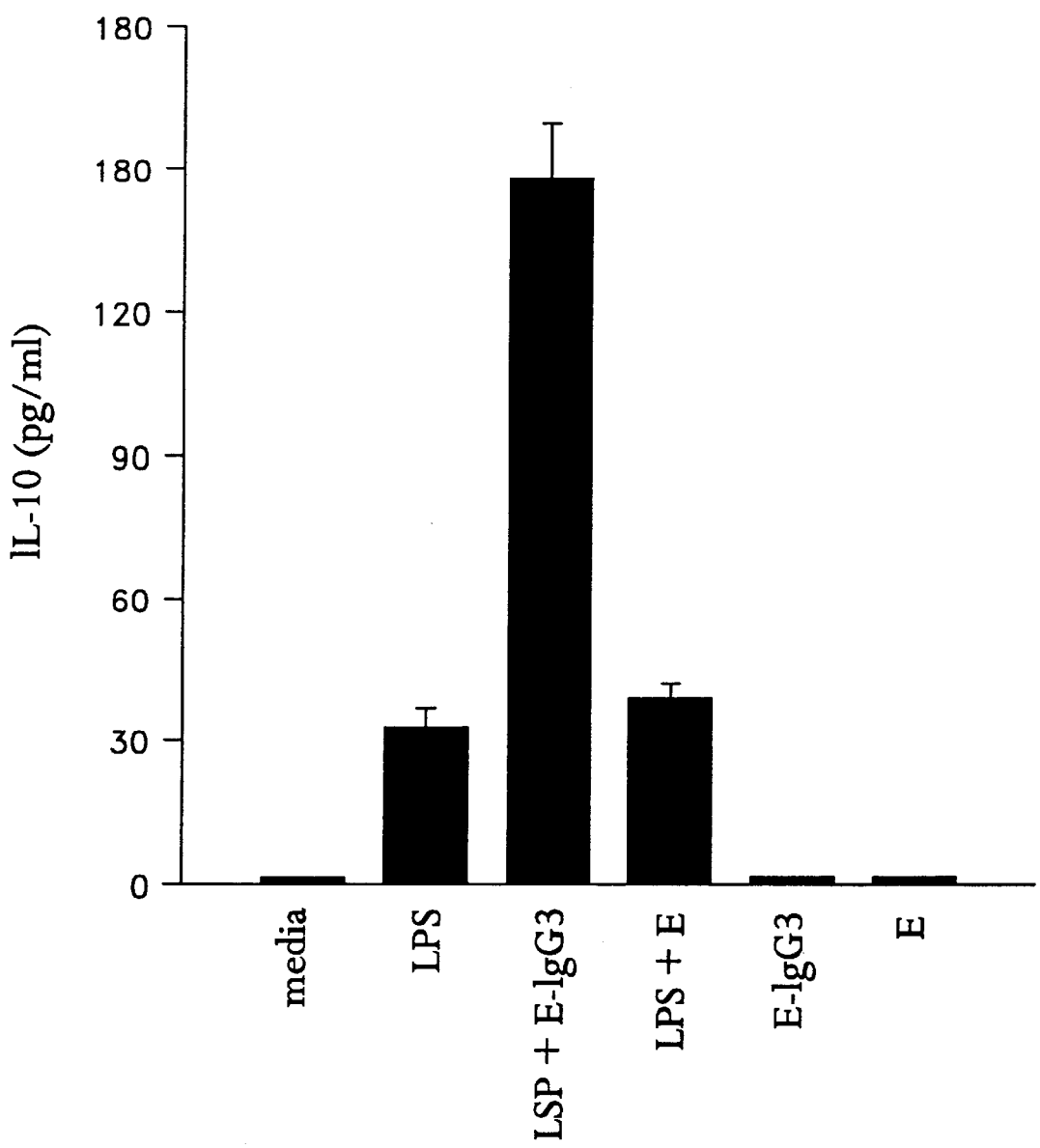
FIG. 4 is a graph of the ELISA determination of IL-10 in the supernatant of murine BMMΦ exposed to either media, IgG3-opsonized sheep erythrocytes (E-IgG3), E, or LPS alone, or LPS in combination with either E-IgG3 or E.

Stimulation of macrophages with LPS and E-IgG3 induced a 5-fold increase in IL-10 production relative to stimulation with LPS alone (FIG. 4).

EXAMPLE 4

Suppression of Macrophage IL-12 Production by LPS/Fcγ-induced IL-10

The following demonstrates that the levels of IL-10 that were produced by macrophages in response to FcγRI coligation is adequate to suppress IL-12 production.

A. Macrophage Stimulation and IL-12 ELISA

Supernatants from BMMΦ exposed to either media or LPS in combination with E-IgG for 24 hours were harvested and filtered through a 0.2 μm filter. Supernatants were diluted 1:3 with media and incubated for 15 minutes at 4° C. either in the presence or absence of a neutralizing mAb to IL-10 (JESS-2A5; 20 μg/ml). Diluted supernatants were then added to BMMΦ, that had been primed with IFNγ (100 U/ml) for 8 hours, and immediately treated with LPS. After 24 hours the supernatant was harvested and IL-12(p70) levels were determined by ELISA using mAbs C18.2 (anti-murine IL-12 p35) and C17.15 (biotinylated anti-murine IL-12 p40) as ELISA capture and detection antibodies, respectively, according to protocols provided by PharMingen (San Diego, Calif.). Recombinant murine IL-12 (Genzyme Corp.) was used as a standard. mAbs C18.2 and C17.15 were purified from ascitic fluid (The Wistar Institute, Philadelphia, Pa.).

B. Results

Figure 5:
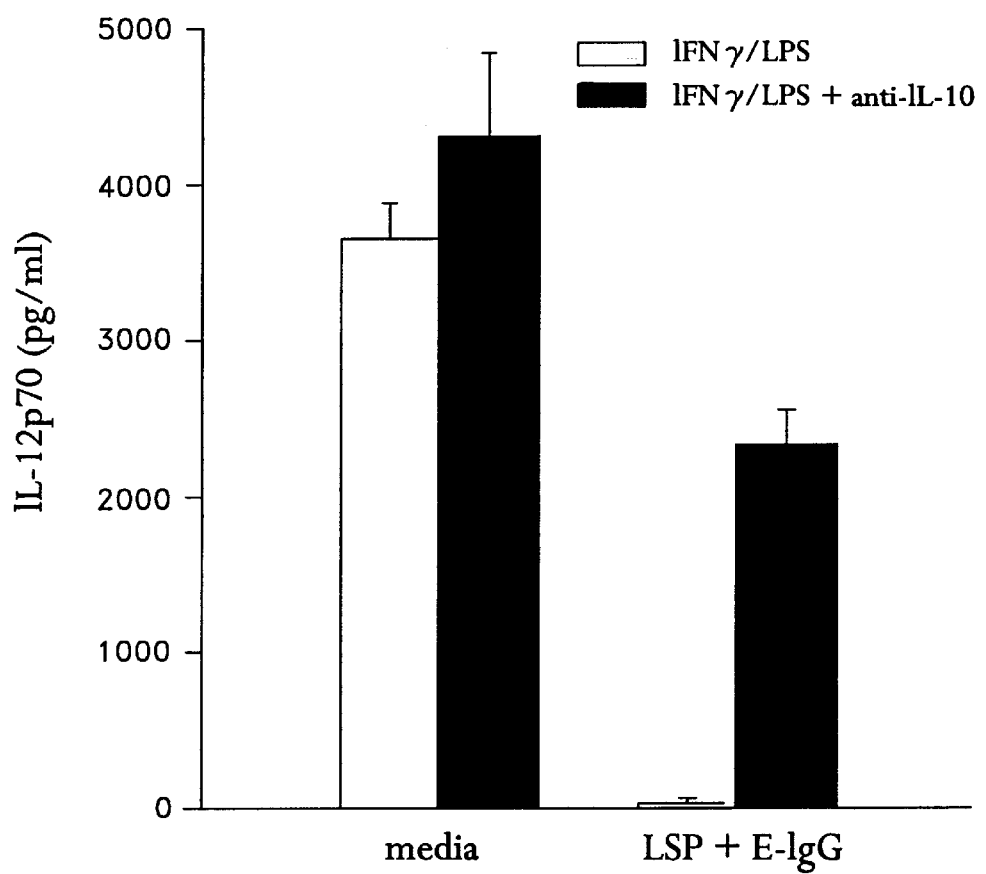
FIG. 5 is a graph of the ELISA determination of IL-12 (p70) in the supernatant of murine BMMΦ. The test supernatant was generated by (i) priming the test BMMΦ with IFNγ, (ii) treating the test BMMΦ with another BMMΦ supernatant, which other BMMΦ supernatant was generated by exposing BMMΦ to either media alone or LPS in combination with E-IgG, followed by incubation of the supernatant in the presence or absence of a neutralizing monoclonal antibody to IL-10 (anti-IL-10,), and (iii) treating the test BMMΦ with LPS.

The ELISA results are set forth in FIG. 5. Values represent the mean of three independent experiments, each performed in triplicate, ±SE. The supernatants from LPS/FcγRI-stimulated BMMΦ reduced IL-12 (p70) secretion to near-background levels. Treating these inhibitory supernatants with a neutralizing to IL-10 partially restored IL-12(p70) production. These results indicate that the IL-10 that is produced by macrophages following LPS/FcγR-stimulation is adequate to inhibit the production of IL-12 by IFNγ-primed macrophages.

EXAMPLE 5

Modulation of Macrophage Proinflammatory Responses by IG-Opsonized LPS Ligation of Fcγ Receptors Cytokine production by macrophages in response to potential proinflammatory stimuli was examined following FcγR ligation.

A. Macrophage Stimulation and Cytokine ELISA

BMMΦ were exposed to either media, LPS, or IgG-LPS. After 24 hours, the supernatant was harvested, and IL-10 and IL-12(p40) levels were determined by ELISA. Murine IL-10 levels were determined, as above, with a mouse IL-10 ELISA kit (Genzyme or Biosource International). Murine IL-12(p40) levels were measured with a mouse IL-12 ELISA kit (Biosource International) according to the manufacturer's instructions.

B. Results

The ELISA results are set forth in FIGS. 6A and 6B. Determinations were performed in triplicate, and values are expressed as the means ±SD. Results are representative of four separate experiments. As expected, LPS induced a potent proinflammatory response by macrophages characterized by moderate levels of IL-10 (FIG. 6A) and high levels of IL-12(p40) (FIG. 6B). In contrast to this, IgG-opsonized LPS induced a different cytokine response, characterized by higher levels of IL-10 (FIG. 6A) and only modest levels of IL-12(p40) (FIG. 6B).

EXAMPLE 6

Modulation of Macrophage Proinflammatory Responses by IgG-Opsonized LPS Ligation of Fcγ Receptors Similar studies were performed using the Gram-negative bacterium *H. influenzae*. Cytokine production by macrophages in response to stimulation with unopsonized or IgG-opsonized *H. influenza* was examined following FcγR ligation.

A. Opsonization of Heat-killed Bacteria

The Eagan clinical isolate of type-b *Haemophilus influenzae* has been previously described and characterized (Noel et al., *J. Inf. Dis.* 166:178–182, 1992). Organisms were grown for 3 hours at 37° C. in brain-heart infusion broth (Difco, Detroit, Mich.) supplemented with NAD and hemin and then washed twice in HBSS. Bacteria were heat killed by incubating at 60° C. for 15 minutes. Bacteria were opsonized by incubation with anti-*H. influenzae* polyserotype antiserum (Difco) at a 1:25 dilution for 15 minutes at room temperature.

B. Macrophage Stimulation and Cytokine ELISA

BMMΦ were incubated with media alone or with equal numbers (130 bacteria per macrophage) of either unopsonized or opsonized heat-killed *H. influenzae*. After 24 hours, the supernatant was harvested, and IL-10 and IL-12 (p40) levels were determined by ELISA.

C. Results

The ELISA results are set forth in FIG. 7A (IL-10) and 7B (IL-12(p40)). Determinations were performed in triplicate, and values are expressed as the means±SD. Results are representative of three separate experiments. Unopsonized *H. influenzae* induced the production of relatively high levels of both IL-10 (FIG. 7A) and L-12(p40) (FIG. 7B). IgG-opsonized bacteria, however, induced a significant decrease in the production of IL-12(p40) protein, and an increase in the production of IL-10. Thus, in both the sheep erythrocyte and bacteria in vitro models, the ligation of FcγR by opsonization with IgG resulted in a reduction in macrophage proinflammatory responses.

EXAMPLE 7

Modulation of In Vivo Responses to Bacterial Endotoxin

Studies similar to the in vitro studies performed above were repeated in experimental animals. These studies were performed in RAG-1$^{-/-}$ mice, since recent studies have demonstrated that normal mice have naturally occurring antibodies to LPS (Reid et al., *J. Immunol.* 159:970–975, 1997). IgG opsonization of LPS reversed the inflammatory cytokine response to LPS in vivo.

A. In Vivo Challenge with IgG-opsonized LPS and Cytokine ELISA

RAG-1$^{-/-}$ mice (The Jackson Laboratory, Bar Harbor, Me.) received either IgG-LPS or LPS intravenously (tail vein) at a final LPS dose of 4 μg per mouse. Control LPS was incubated with an equal volume of HBSS. Mice were bled by retroorbital puncture at the time intervals up to 24 hours indicated in FIGS. 8A and 8B, and serum cytokine levels were determined by ELISA. In another experiment, serum was assayed for cytokines by ELISA at 2, 4 and 8 hours.

B. Results

The ELISA results of the 24 hour study are set forth in FIGS. 8A and 8B. Data show the mean±SD of groups of four separately handled mice. *P<0.01, and ***P<0.08 (significant by Rank-Sum Analysis) versus the LPS-treated group as determined by the Student's t test. The ELISA results of the 8-hour study are set forth in FIGS. 9A and 9B. Data show the mean±SD of groups of five separately handled mice. The injection of low level (4 μg) of LPS into the RAG-1$^{-/-}$ mice induced the transient production of relatively high levels of serum IL-12(p40) (FIGS. 8A, 9A), and only modest levels of IL-10 (FIGS. 8B, 9B). The observation that RAG-1$^{-/-}$ mice make high amounts of IL-12 in response to low levels of LPS is consistent with previous observations that antibody-deficient mice are hypersusceptible to LPS (Reid et al., *J. Immunol.* 159:970–975, 1997). The injection of IgG-opsonized LPS into these mice induced an alteration in cytokine profile. RAG-1$^{-/-}$ mice injected with IgG-LPS made only modest levels of IL-12, but they more than doubled their production of IL-10. This reciprocal alteration in the pattern of cytokine production suggests that IgG opsonization of LPS not only increases the rate of LPS clearance through FcγR, but in doing so also mediates a desirable effect by dampening the proinflammatory response of IL-12 production.

EXAMPLE 8

Passive Immunization with Anti-LPS Antibody

Mice were injected intraperitoneally with 100 μl of anti-LPS antibody (Calbiochem) 2 or 18 hours before being injected intravenously with LPS (4 μg, E. coli 0128:B12). Control uninjected mice received LPS alone. Serum was collected at 2, 4, and 8 hours post LPS injection and assayed for IL-12(p40) production as in FIG. 10A (solid circles, IL-12 for mice injected with anti-LPS two hours before LPS injection; solid triangles, IL-12 for mice injected with anti-LPS eighteen hours before LPS injection; open circles, IL-12 for control mice receiving LPS alone). IL-10 production in serum collected 2 hours post LPS injection is shown in FIG. 10B. Symbols in the figures represent mean serum cytokine levels from 5 mice±SD.

The data indicate that the prophylactic administration of antibody before endotoxemia can prevent the production of inflammatory cytokines.

All references cited herein are incorporated by reference.

The present invention may be embodied in other specific forms without departing from the spirit or essential attributes thereof and, accordingly, reference should be made to the appended claims, rather than to the foregoing specification, as indication the scope of the invention.

What is claimed is:

1. A method for enhancing IL-10 production by FcγRI receptor-expressing cells of a mammal comprising administering to the mammal an effective amount of a ligating agent which causes ligation of FcγRI receptors on the FcγI receptor-expressing cells, wherein the ligating agent comprises (i) at least two IgG Fc regions or (ii) a multivalent antibody which binds to FcγI receptor.

2. The method according to claim 1, wherein the mammal is a human being.

3. The method according to claim 1, wherein the FcγRI receptor-expressing cells comprise macrophages.

4. The method according to claim 3, wherein the ligating agent does not cause ligation of FcγRIII receptors.

5. The method according to claim 1, wherein the multivalent antibody which binds to FcγRI receptor is a monoclonal antibody.

6. The method according to claim 3, wherein the ligating agent comprises an immune complex containing at least two antibody molecules or fragments thereof which contain the Fc region of IgG.

7. The method according to claim 3, wherein the ligating agent comprises an antibody multimer containing at least two antibody molecules or fragments thereof which contain the Fc region of IgG.

8. The method according to claim 7, wherein the antibody multimer comprises IgG dimers, IgG trimers, or a combination thereof.

9. The method according to claim 8, wherein the antibody multimer comprises, on a weight percent basis, at least about 50% IgG dimers, IgG trimers, or a mixture thereof.

10. The method of claim 1, wherein the ligating agent is a synthetic or recombinant peptide.

* * * * *